(12) United States Patent
Martos-Sánchez et al.

(10) Patent No.: US 11,662,312 B2
(45) Date of Patent: May 30, 2023

(54) POLYSORBATE QUANTIFICATION ASSAY

(71) Applicant: CORIOLIS PHARMA RESEARCH GMBH, Martinsried (DE)

(72) Inventors: Ariadna Martos-Sánchez, Munich (DE); Andrea Hawe, Munich (DE)

(73) Assignee: CORIOLIS PHARMA RESEARCH GMBH, Martinsried (DE)

( * ) Notice: Subject to any disclaimer, the term of this patent is extended or adjusted under 35 U.S.C. 154(b) by 114 days.

(21) Appl. No.: 16/624,730

(22) PCT Filed: Jun. 26, 2018

(86) PCT No.: PCT/EP2018/067117
§ 371 (c)(1),
(2) Date: Dec. 19, 2019

(87) PCT Pub. No.: WO2019/002295
PCT Pub. Date: Jan. 3, 2019

(65) Prior Publication Data
US 2021/0156801 A1    May 27, 2021

(30) Foreign Application Priority Data
Jun. 27, 2017 (EP) .................................. 17178071

(51) Int. Cl.
*G01N 21/64*    (2006.01)
*G01N 33/15*    (2006.01)

(52) U.S. Cl.
CPC ........... *G01N 21/643* (2013.01); *G01N 33/15* (2013.01); *G01N 2021/6439* (2013.01)

(58) Field of Classification Search
None
See application file for complete search history.

(56) References Cited

U.S. PATENT DOCUMENTS

2005/0208534 A1    9/2005    Dallwig et al.

FOREIGN PATENT DOCUMENTS

| EP | 2799866 | 11/2014 |
|---|---|---|
| EP | 2990778 | 3/2016 |
| JP | H05-256784 | 10/1993 |
| JP | 2003-075349 | 3/2003 |
| JP | 2007-532886 | 11/2007 |
| JP | 2009-510392 | 3/2009 |
| JP | 2013-517309 | 5/2013 |
| JP | 2015-533218 | 11/2015 |
| JP | 2016-048203 | 4/2016 |
| JP | 2017-067605 | 4/2017 |

(Continued)

OTHER PUBLICATIONS

Cheng, C. et al. Fluorescentlabelingofdendriticspinesincellcultures withthecarbocyaninedye"DiI", Frontiers in Neuroanatomy, vol. 8, Article 30, (Year: 2014).*

(Continued)

*Primary Examiner* — Xiaoyun R Xu
(74) *Attorney, Agent, or Firm* — Parker Highlander PLLC

(57) ABSTRACT

The present invention relates to a method for the quantification of a polysorbate in a sample, comprising the steps of a) providing a sample, comprising at least one polysorbate; b) combining the sample with a carbocyanine dye; c) measuring fluorescence of the mixture; and d) correlating said fluorescence with the amount of polysorbate.

19 Claims, 13 Drawing Sheets

A

B

C

(56) References Cited

FOREIGN PATENT DOCUMENTS

| WO | WO03/091693 | 11/2003 |
|----|-------------|---------|
| WO | WO2005/113147 | 12/2005 |
| WO | WO2011/089062 | 7/2011 |
| WO | WO2014/058760 | 4/2014 |

OTHER PUBLICATIONS

"CMC-535™ Detergent Assay: A Fluorescent Detergent Assay for Assaying Detergents Below Their CMC Values", G-Biosciences dated Jun. 18, 2015, retrieved from the internet: www.gbiosciences.com/image/pdfs/protocol/D535_protocol.pdf on Jul. 19, 2018.

"RediPlate™ 96 RiboGreen© RNA Quantitiation Kit (R-32700)", Molecular Probes, dated 2003.

International Search Report and Written Opinion issued in International Application No. PCT/EP2018/067117, dated Jul. 19, 2018.

Westmark, Cara J., et al. "Reversal of fragile X phenotypes by manipulation of AβPP/Aβ levels in Fmr1 KO mice." *PloS one* 6.10 (2011): e26549.

Zheng, Songyan, et al. "Sensitive fluorescence-based method for the rapid determination of polysorbate-80 content in therapeutic monoclonal antibody products." *Pharmaceutical development and technology* 20.7 (2015): 872-876.

Martos et al., "Trends on Analytical Characterization of Polysorbates and Their Degradation Products in Biopharmaceutical Formulations," *Journal of Pharmaceutical Sciences*, 106(7): 1722-1735, 2017.

Martos et al., Novel High-Throughput Assay for Polysorbate Quantification in Biopharmaceutical Products by Using the Fluorescent Dye DiI, *Journal of Pharmaceutical Sciences*, 109 (1): p. 646-655, 2020.

Office Communication issued in correspondence Japanese Application No. 2019-572526 dated Apr. 18, 2022 {English translation}.

* cited by examiner

A

B

C

A

B

A

B

A

B

POLYSORBATE QUANTIFICATION ASSAY

The present application is a national phase application under 35 U.S.C. § 371 of International Application No. PCT/EP2018/067117, filed Jun. 26, 2018, which claims priority from European Application number 17178071.1, filed on Jun. 27, 2017, the content of each of which is hereby incorporated by reference in its entirety.

BACKGROUND OF THE INVENTION

Polysorbates are a family of non-ionic surfactants widely used as excipients in pharmaceutical products and in the food industry. Polysorbate 20 (PS20) and polysorbate 80 (PS80)—also known as Tween® 20 and Tween® 80—are the most common surfactants used to protect therapeutic proteins against adsorption to interfaces and related instabilities. The contribution of PS20 and PS80 to protein stabilization in biopharmaceutical products is well accepted, and both are excipients for parenteral administration approved by regulatory agencies. A majority of biopharmaceutical products containing peptides, proteins, antibodies and vaccines are formulated with polysorbates. For example, about 80% of the commercial monoclonal antibodies (MAbs) contain PS20 or PS80. Their high hydrophilic-lipophilic balance (HLB) value and low critical micelle concentration (CMC) account for their high surface activity even at low concentrations. Typical polysorbate concentrations in biopharmaceuticals are between 0.001 and 0.1% (w/v), corresponding to 0.01 and 1 mg/ml.

Although the molecular details of stabilization are not yet fully understood, polysorbates are known to contribute to protein stability by two different mechanisms, i.e., through (i) competitive adsorption to the hydrophobic interfaces and/or (ii) direct binding to the protein. In the first case, polysorbates show higher adsorption energies per unit area than proteins, thereby efficiently competing with proteins and protecting them against adsorption to hydrophobic interfaces. Moreover, polysorbates may interact directly with the protein increasing its stability in solution by binding to and protecting exposed hydrophobic regions. This prevents aggregation by reducing protein-protein interactions. Which of these two mechanism prevails within the stabilization of a particular protein is protein- and polysorbates-dependent.

Polysorbates are amphiphilic structures. Their hydrophilic fraction comprises a sorbitan head group with each of the hydroxyl groups being bound to a polyethylene glycol chain (PEG/polyethylene oxide chain/POE). The hydrophobic one is featured by fatty acids (FA) esterified in their hydroxyl groups. Theoretically, the different polysorbates can be differentiated by those fatty acids. In reality, commercially available polysorbate contains structurally related molecules and only approximately 20% (w/w) of the total polysorbate material comply with the theoretical molecular structure.

Besides by-products formed during synthesis, degradation reactions (oxidation and hydrolysis) may also contribute to the heterogeneity of polysorbate solution. The formation of polysorbate degradation products could result in a loss of surfactant concentration within the formulation.

Apart from that, their surfactant properties may be lost. This could potentially affect protein stability and moreover, result in the formation of protein aggregates and particles. Thus, degradation reactions have to be prevented. A general overview of degradation of polysorbates and the analysis of their degradation may be found in Martos, A. et. al.; Journal of Pharmaceutical Sciences; 2017; doi: 10.1016/j.xphs.2017.03.001.

As it is crucial to monitor the polysorbate concentration within therapeutic protein formulations, as well as polysorbate degradation, several techniques have been developed to analyse polysorbate contents of samples, as well as the content of their degradation products. In general, after sample preparation to remove protein (e.g. by protein precipitation with organic solvents or solid phase extraction), the sample is subjected to reverse phase liquid chromatography (RP-HPLC) in order to separate the sample components (polysorbate species) and prepare them for further analysis, by applying mass spectroscopy, ELSD or CAD detection. Furthermore, UV/Vis detection may be applied after hydrolysis and release of oleic acid for polysorbate 80. Most of these methods are complex and time consuming, and sensitive to the interference by protein. Next to this fluorescent dye approaches are applied for quantification purpose. The most common assay is the fluorescence micelle assay (FMA) based on N-phenyl-1-naphtylamine (NPN), which is based on the interaction of the fluorescent dye with hydrophobic environment present in particular in micelles above the CMC. The drawback of the assay is the lack of specificity for PS (i.e. NPN may interact with protein, silicone oil and may be influenced by solution viscosity), and that quantification of PS is only feasible at concentrations above the CMC.

As such it was an object of the present invention to provide a new method which would allow for rapid and ideally automated or semi-automated detection and quantification of polysorbates.

SUMMARY OF THE INVENTION

The inventors surprisingly found that the amount of polysorbate in a sample can be accurately quantified by using a carbocyanine dye, in particular carbocyanine dyes selected from 1,1'-dioctadecyl-3,3,3',3'-tetramethyl-indocarbocyanine perchlorate (DiI) or its derivatives DiD (1,1'-Dioctadecyl-3,3,3',3'-Tetramethylindodicarbocyanine 4-Chlorobenzenesulfonate) and DiO (3,3'-dioctadecyloxacarbocyanine perchlorate).

Accordingly, in a first aspect the invention relates to a method for the quantification of polysorbates in a sample, comprising the steps of:
a) providing a sample, comprising at least one polysorbate;
b) combining the sample with a carbocyanine dye;
c) measuring fluorescence of the mixture; and
d) correlating said fluorescence with the amount of polysorbate.

In a further aspect, the invention relates to the use of a carbocyanine dye for the quantification of polysorbates in a sample.

The invention also relates to a well-plate, such as a 96-well plate, wherein at least some wells or even each well comprises a defined amount of a carbocyanine dye.

In an additional aspect, the invention relates to a kit for the quantification of polysorbates in a sample comprising:
a) a carbocyanine dye;
b) a dilution buffer;
c) optionally calibration samples.

In a specific embodiment, the kit comprises a well plate comprising a defined amount of carbocyanine dye in each well.

(A) PS20-DiI-fluorescence emission spectra (Excitation (Exc.) at 550 nm). Fluorescence spectra (Emission (EM.) 560-620 nm) of different PS20 concentrations (0.0002-0.0025% (w/v)) after the addition of DiI (357 nM). The measurements were performed in a cuvette-based spectrofluorometer: 0% (w/v) PS20 -··-··-, 0.0002% (w/v) PS20 -·-·-·, 0.0003% (w/v) PS20 . . . , 0.0005% (w/v) PS20 - - - -, 0.0009% (w/v) PS20 - - - -, 0.0015% (w/v) PS20 -------, 0.0025% (w/v) PS20 ------- .

(B) Magnification of low intensity range of (A).

(C) PS20-DiI-calibration curves (0.0008-0.0021% (w/v)) at 615 nm. Maximum fluorescence intensities observed plotted against the corresponding PS20 concentrations.

Figure 3:
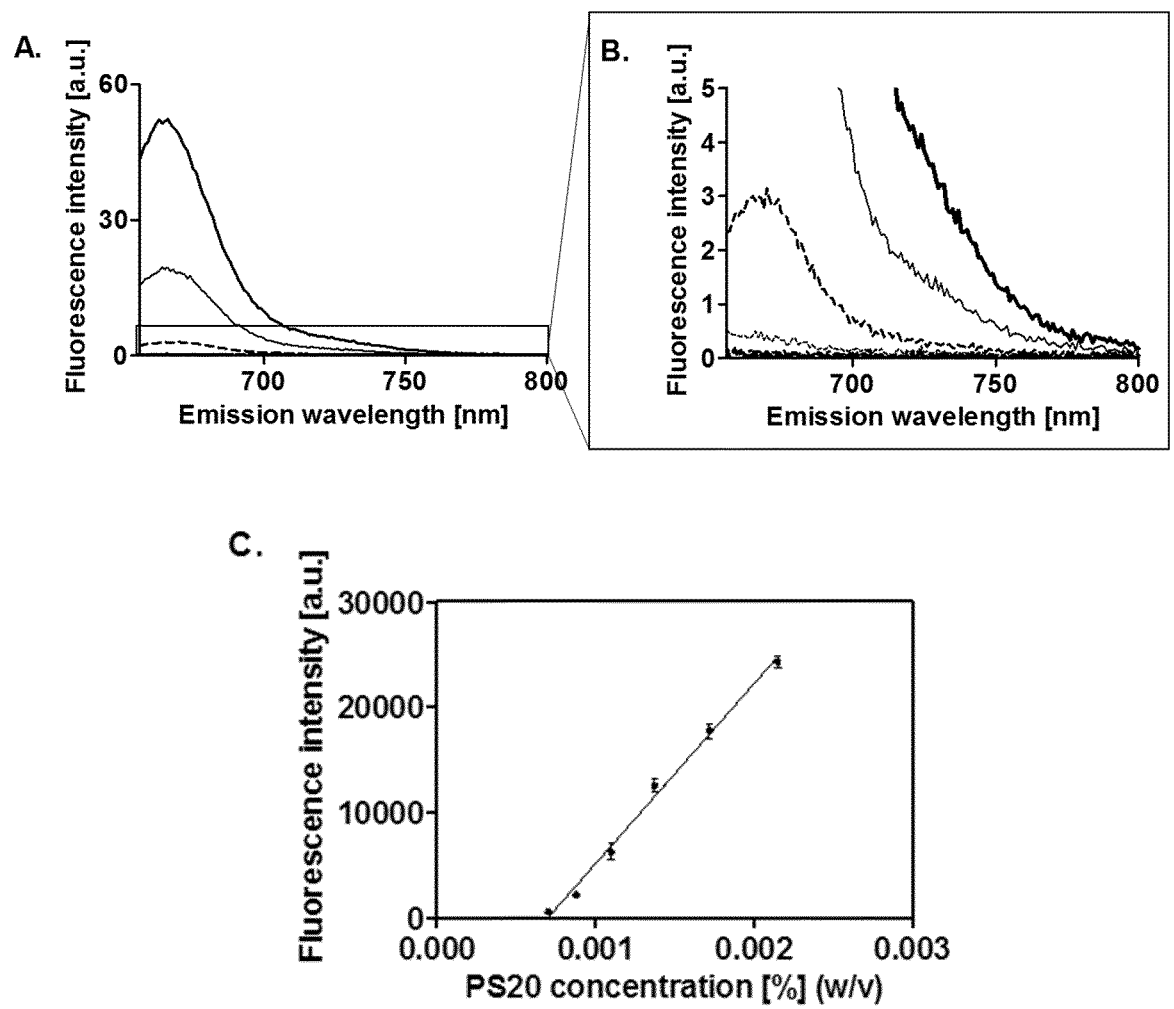

FIG. 3: Fluorescence emission properties of PS20 in presence of DiD.

(A) PS20-DiD-fluorescence emission spectra (Exc. 646 nm). Fluorescence spectra (656-800 nm) of different PS20 concentrations (0.0002-0.0025% (w/v)) after the addition of DiD (357 nM). The measurements were performed in a cuvette-based spectrofluorometer: 0% (w/v) PS20 -··-··-, 0.0002% (w/v) PS20 -·-·-·, 0.0003% (w/v) PS20 . . . , 0.0005% (w/v) PS20 - - - -, 0.0009% (w/v) PS20 - - - -, 0.0015% (w/v) PS20 -------, 0.0025% (w/v) PS20 ------- .

(B) Magnification of low intensity range of (A).

(C) PS20-DiD-calibration curve (0.0008-0.0021% (w/v)) at 665 nm. Maximum fluorescence intensities observed plotted against the corresponding PS20 concentrations.

Figure 4:
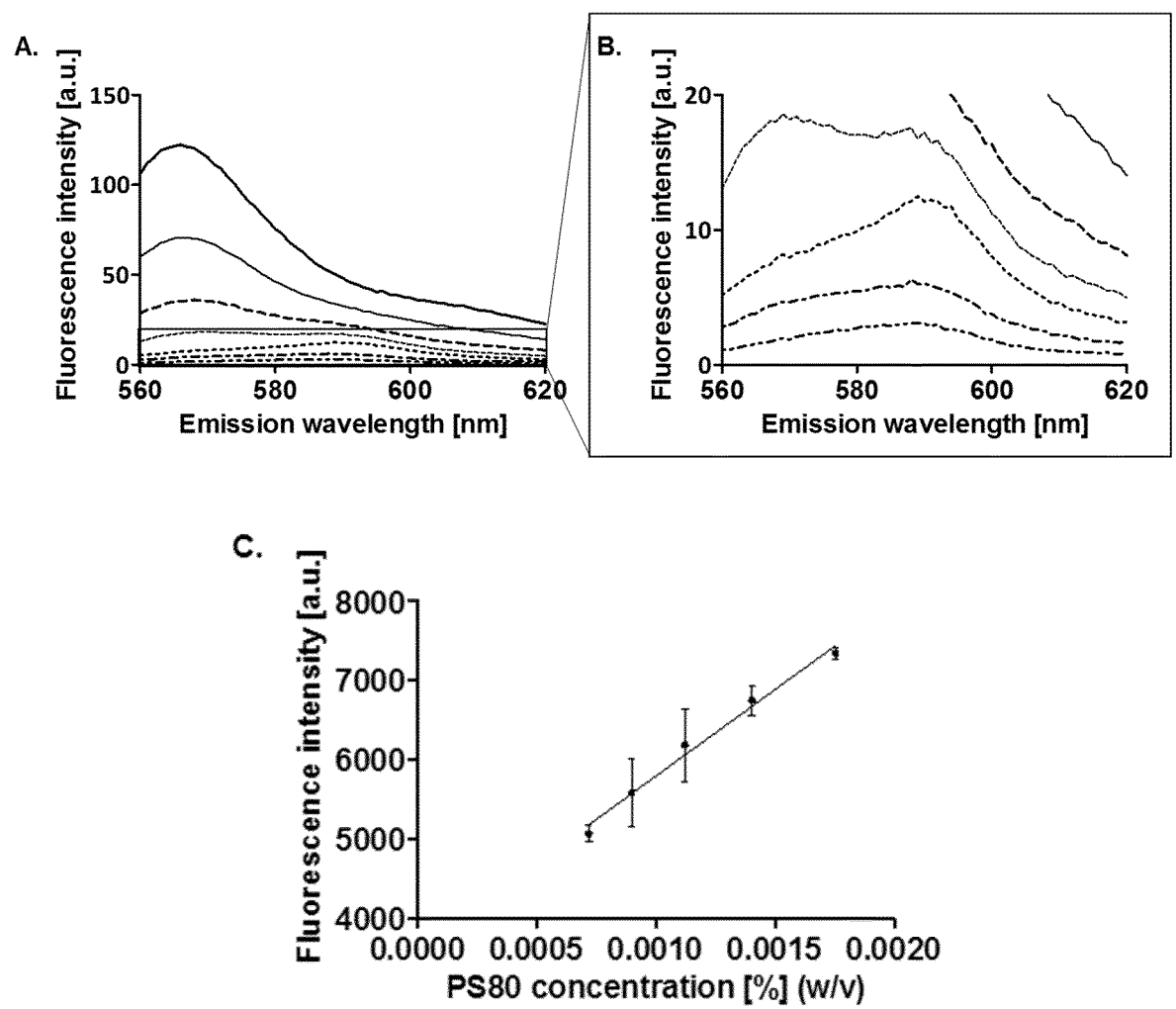

FIG. 4: Fluorescence emission properties of polysorbate 80 (PS80) in the presence of DiI.

(A) PS80-DiI-fluorescence emission spectra (Exc. 550 nm). Fluorescence spectra (560-620 nm) of different PS80 concentrations (0.0002-0.0025% (w/v)) after the addition of DiI (357 nM). The measurements were performed in a cuvette-based spectrofluorometer: 0% (w/v) PS80 -··-··-, 0.0004% (w/v) PS80 -·-·-, 0.0006% (w/v) PS80 . . . , 0.0010% (w/v) PS80 - - - -, 0.0016% (w/v) PS80 - - -, 0.0027% (w/v) PS80 -------, 0.0045% (w/v) PS80 ------- .

(B) Magnification of low intensity range of (A).

(C) PS80-DiI-calibration curve (0.0007-0.0018% (w/v)) at 615 nm. Maximum fluorescence intensities observed plotted against the corresponding PS80 concentrations. The measurements were performed in a plate-reader.

Figure 5:
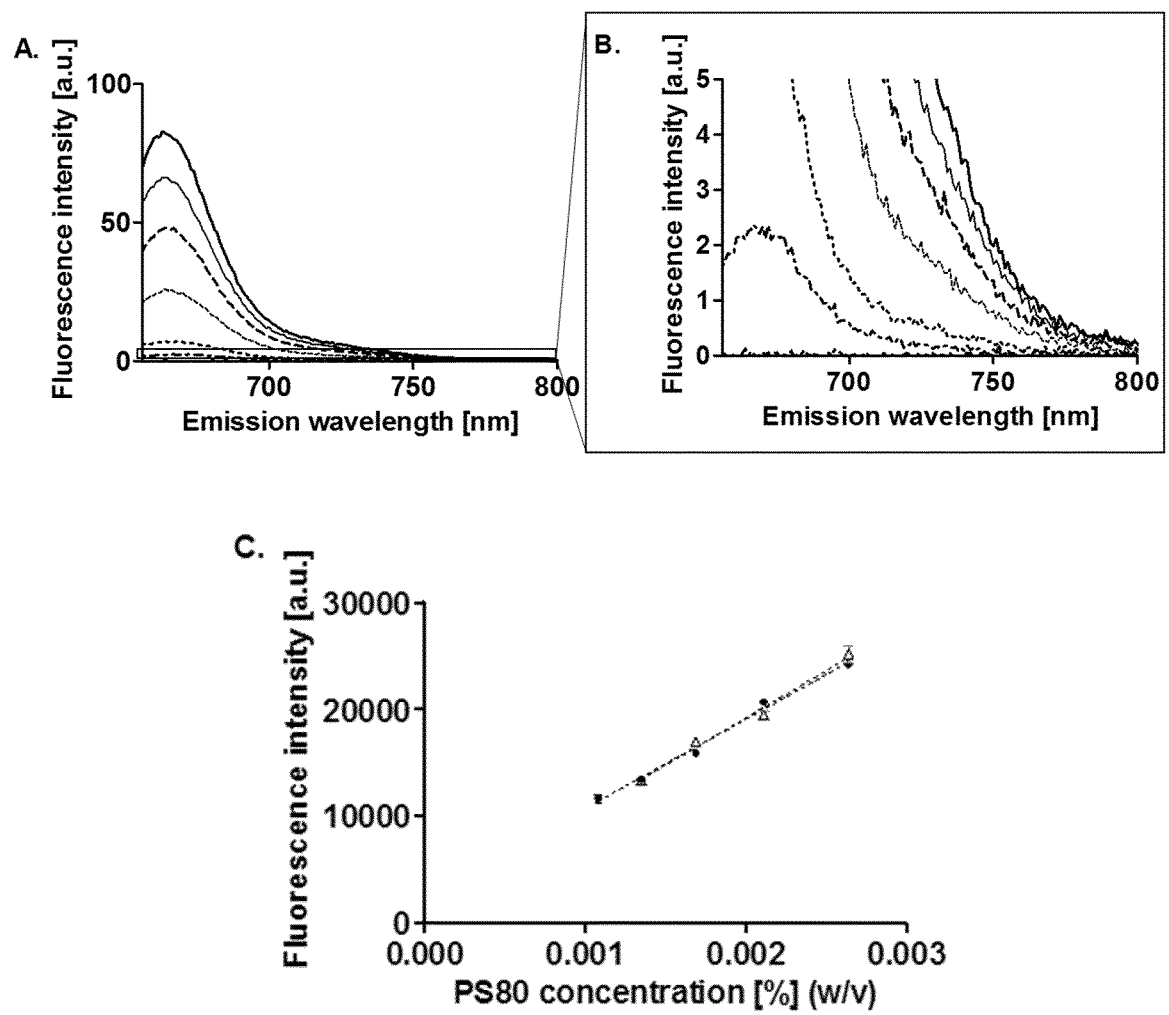

FIG. 5: Fluorescence emission properties of PS80 in presence of DiD.

(A) PS80-DiD-fluorescence emission spectra (Exc. 646 nm). Fluorescence spectra (656-800 nm) of different PS80 concentrations (0.0002-0.0045% (w/v)) after the addition of DiD (357 nM). The measurements were performed in a cuvette-based spectrofluorometer: 0% (w/v) PS80 -··-··-, 0.0004% (w/v) PS80 -·-·-·, 0.0006% (w/v) PS80 . . . , 0.0010% (w/v) PS80 - - - -, 0.0016% (w/v) PS80 - - - -, 0.0027% (w/v) PS80 -------, 0.0045% (w/v) PS80 ------- .

(B) Magnification of low intensity range of (A).

(C) PS80-DiD-calibration curves (-•- 0.0011-0.0026% (w/v) and --Δ-- 0.0014-0.0026% (w/v), respectively) at 665 nm. Maximum fluorescence intensities observed plotted against the corresponding PS80 concentrations. The measurements were performed in a plate reader.

Figure 6:
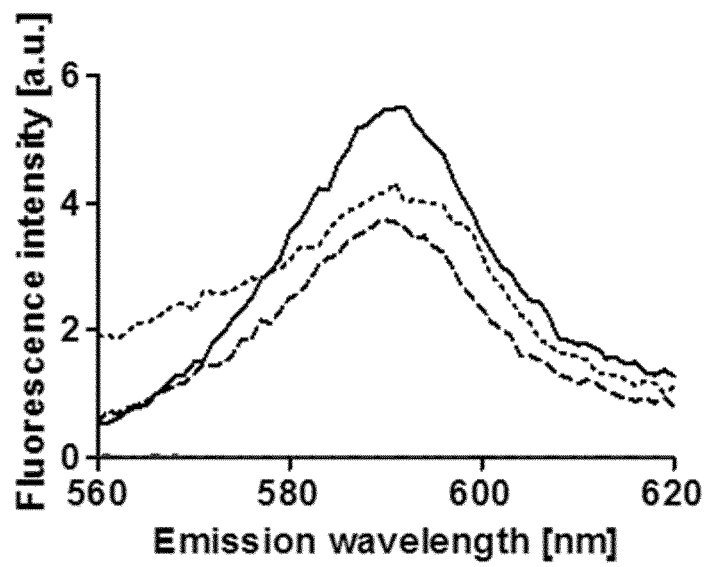

FIG. 6: Influence of silicon oil droplets. Fluorescence emission spectra (560-620 nm) of DiI (357 nM) after excitation at 550 nm measured in a cuvette fluorimeter for water (----), aqueous solution of silicon oil at concentrations of 0.002% (w/v) (- - -) and 0.03% (w/v) ( . . . ).

Figure 7:
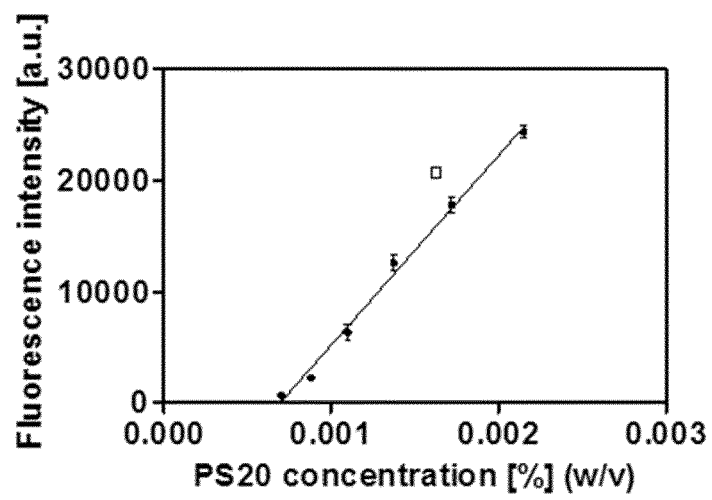

FIG. 7: Calibration curves (prepared without protein --•--) showing the fluorescence emission intensity of DiD (357 nM) at 665, after excitation at 646 nm in a plate-reader. Calibration curve was used for the quantification of PS20 in a sample with a theoretical concentration of 0.00175% (w/v) shown as Q.

Figure 8:
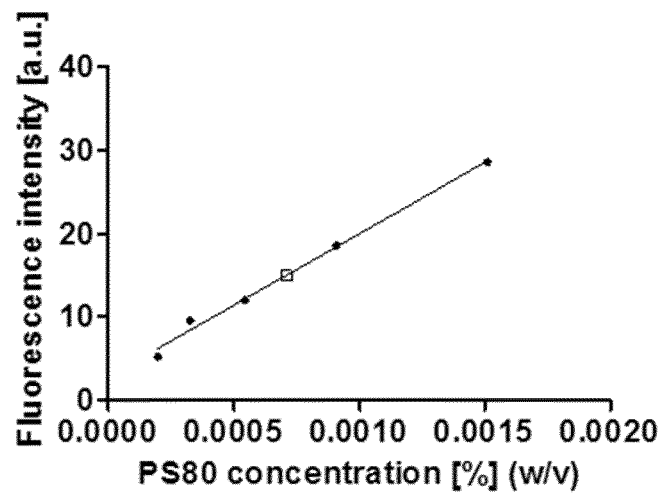

FIG. 8: Calibration curves (prepared without protein --•--) showing the fluorescence emission intensity of DiI (357 nM) at 665, after excitation at 550 nm in a plate-reader. Calibration curve was used for the quantification of PS80 in a sample with a theoretical concentration of 0.0007% (w/v) shown as Q.

Figure 9:
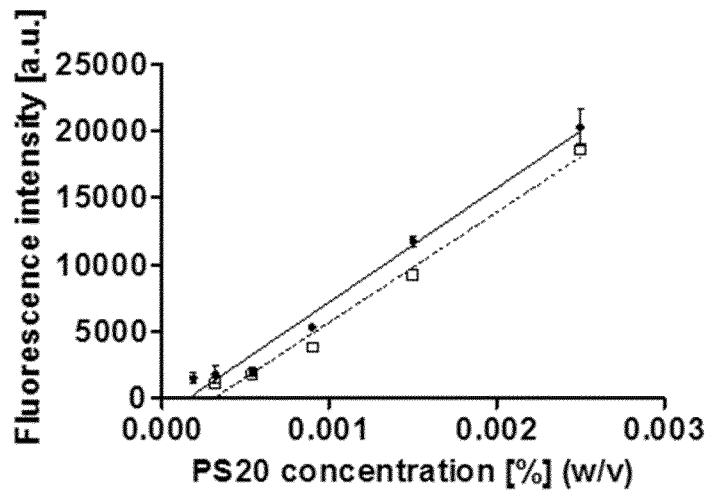

FIG. 9: Calibration curves (prepared without protein --•-- and with 15 mg/mL IgG1 --□--) showing the fluorescence emission intensity of DiI (357 nM) at 615 nm, after excitation at 550 nm in a plate-reader. Calibration curve was used for the quantification of PS20 in samples 1 to 5 with a theoretical concentration of 0.002% (w/v) PS20.

Figure 10:
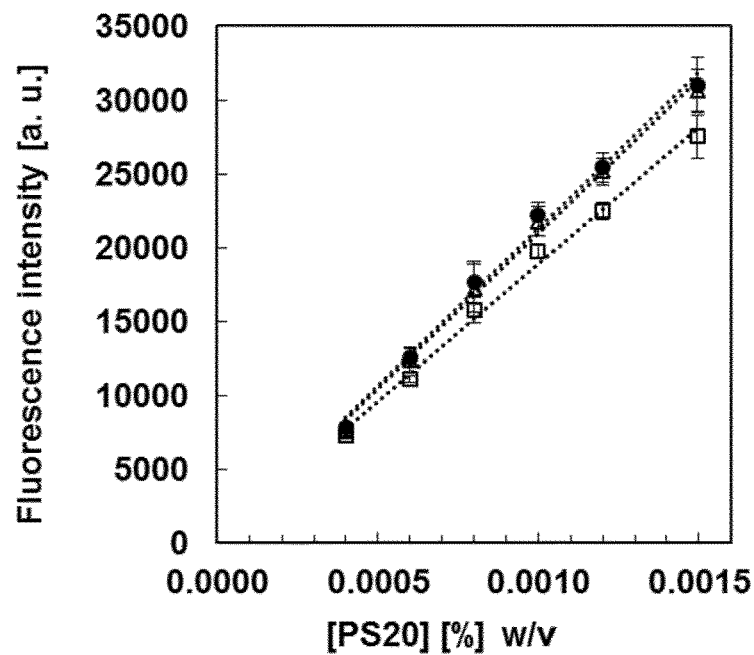
Figure 10:
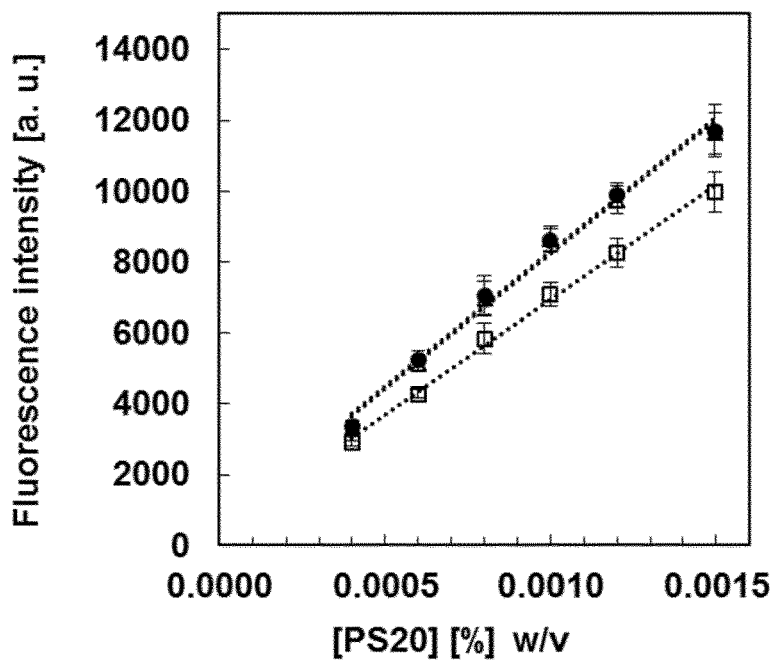

FIG. 10: DiI fluorescence intensity (Exc. 550 nm) after incubation of PS20 samples with 357 nM DiI directly in 96-well plates at 37° C. including shaking (40 rpm).

(A) PS20-DiI-calibration curve (0.0004-0.0015% (w/v)) using emission at 565 nm, measured directly after the addition of DiI at 0 min (□), after 15 min (•) and after 30 min incubation (Δ).

(B) PS20-DiI-calibration curve (0.0004-0.0015% (w/v)) using emission at 615 nm, measured directly after the addition of DiI at 0 min (□), after 15 min (•) and after 30 min incubation (Δ).

Figure 11:
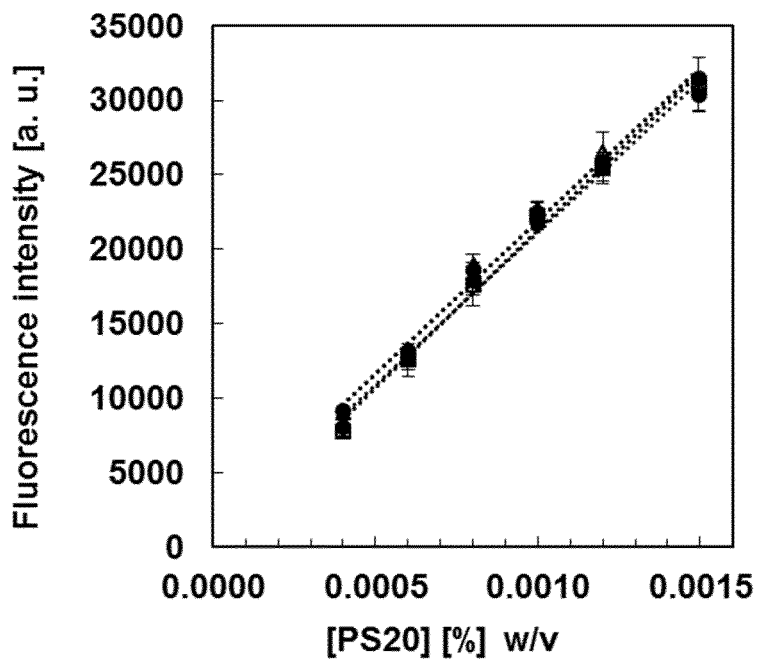
Figure 11:
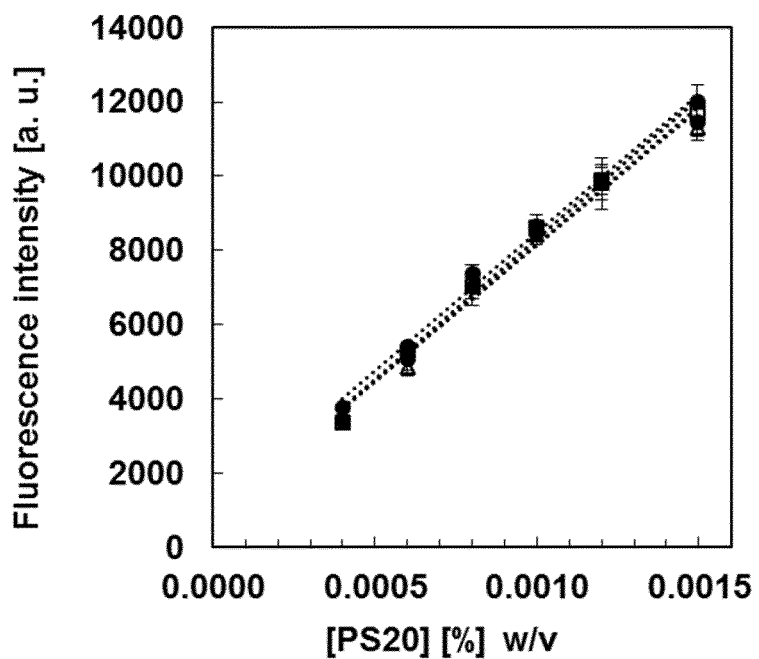

FIG. 11: DiI fluorescence intensity (Exc. 550 nm) after incubation of PS20 samples with 357 nM DiI directly in 96-well plates. Incubation with shaking at 40 rpm at 37° C. (Q). Incubation without shaking at 37° C. (■). Vortexing (•) and incubation at room temperature without shaking (Δ).

(A) PS20-DiI-calibration curves (0.0004-0.0015% (w/v)) using emission at 565 nm.

(B) PS20-DiI-calibration curves (0.0004-0.0015% (w/v)) using emission at 615 nm.

Figure 12:
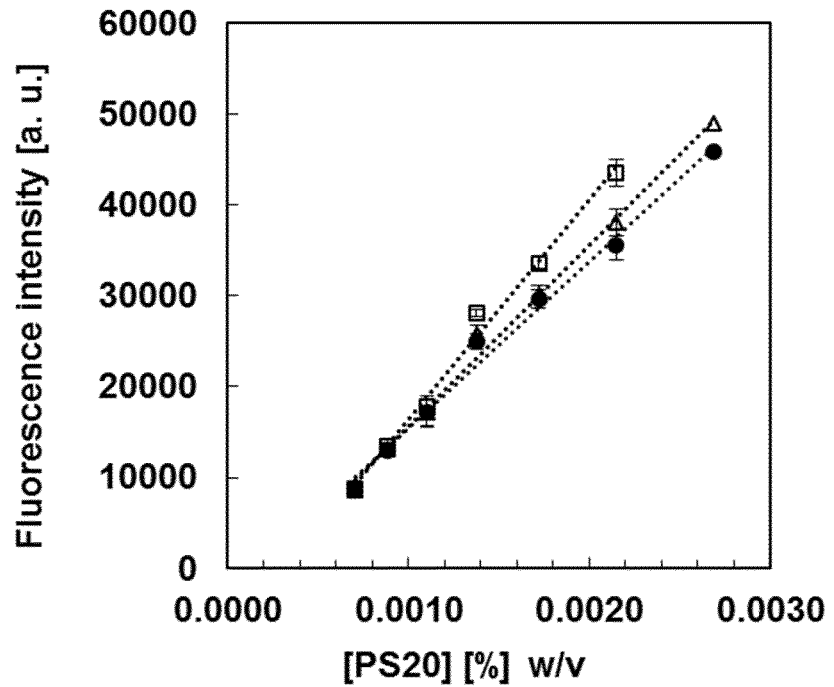

FIG. 12: PS20-DiI-calibration curves (0.0004-0.0030% (w/v)) for three lots of DiI (lot 1 □, lot 2 • and lot 3 Δ). DiI fluorescence intensity (Exc. 550 nm; Em. 565 nm) after incubation of PS20 with 357 nM DiI in 96 well plates for 15 minutes at 37° C. with shaking at 40 rpm.

Figure 13:
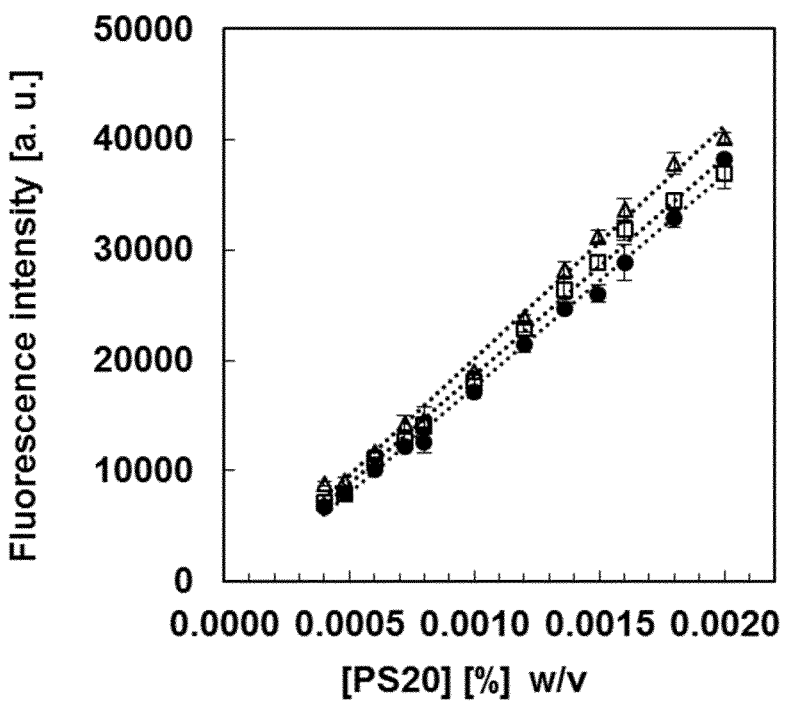

FIG. 13: PS20-DiI-calibration curves (0.0004-0.0020% (w/v)) for three different multicompendial PS20 (□ type 1, • type 2 and Δ type 3). DiI fluorescence intensity (Exc. 550 nm; Em. 565 nm) after incubation of PS20 samples with 357 nM DiI in 96 well plates for 15 minutes at 37° C. with shaking at 40 rpm at 37° C.

Figure 14:
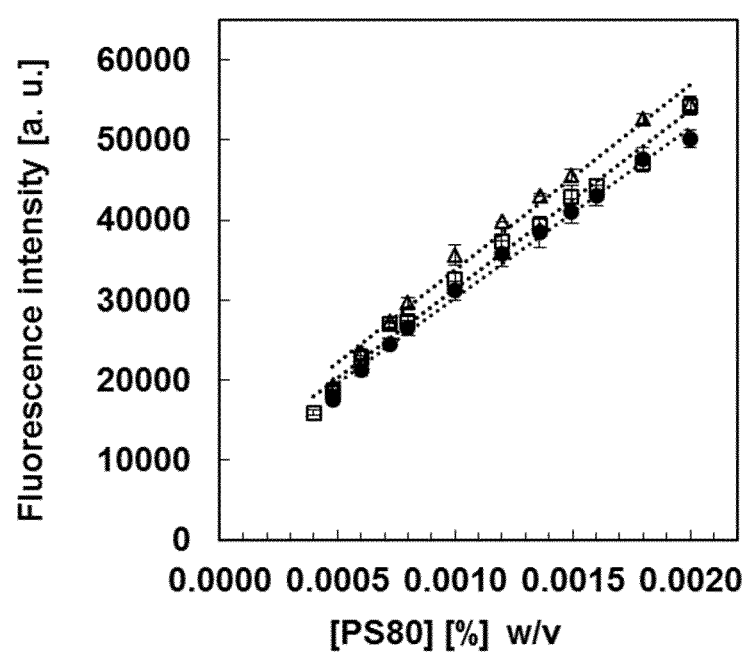

FIG. 14: PS80-DiI-calibration curve (0.0004-0.0020% (w/v)) for three different multicompendial PS80 (□ type 1, • type 2 and Δ type 3). DiI fluorescence intensity (Exc. 550 nm; Em. 565 nm) after incubation of PS80 samples with 357 nM DiI in 96 well plates for 15 minutes at 37° C. with shaking at 40 rpm.

Figure 15:
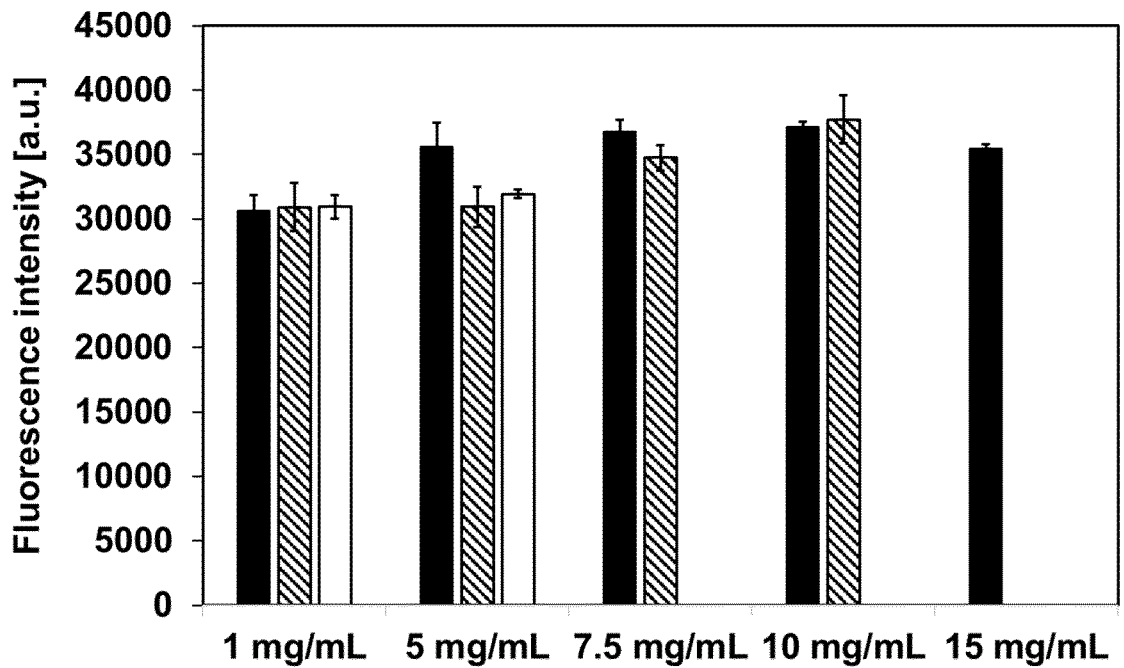
Figure 15:
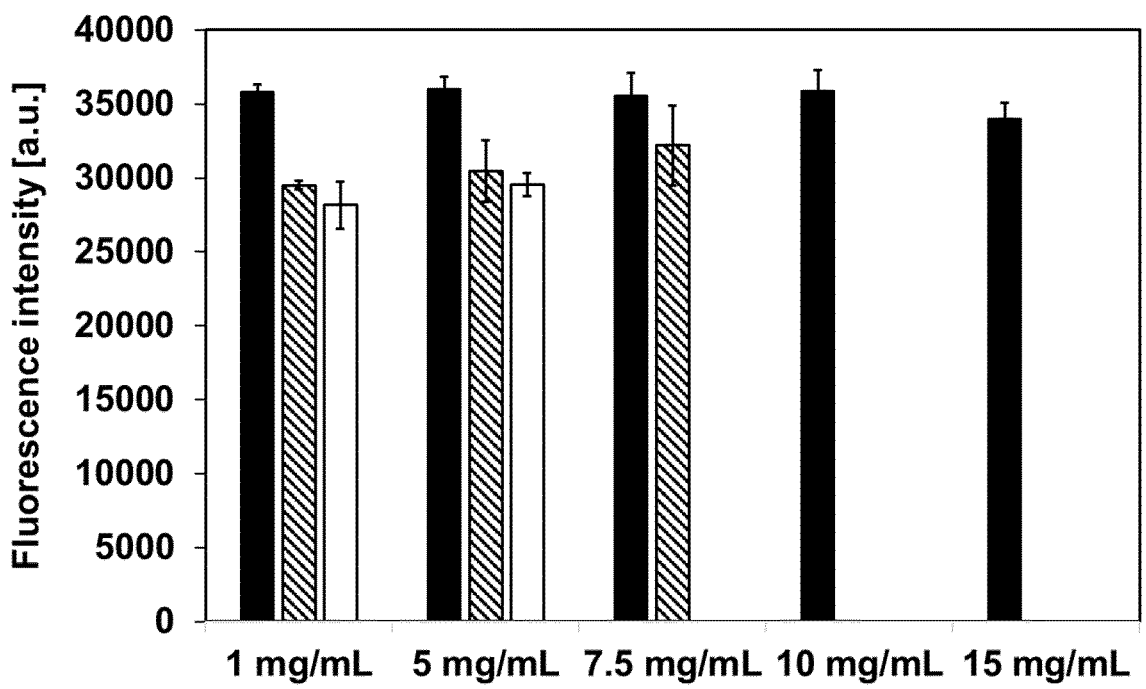

FIG. 15: Fluorescence intensity (Exc: 550 nm, Em: 615 nm) of 350 nM DiI with ~0.006% (w/v) PS20 (A) and PS80 (B) in the presence of different concentrations of 1-15 mg/ml IgG1 (black bars), 1-10 mg/mL Fc-fusion protein (striped bars) and 1-5 mg/ml IgG 3 (white bars).

Figure 16:
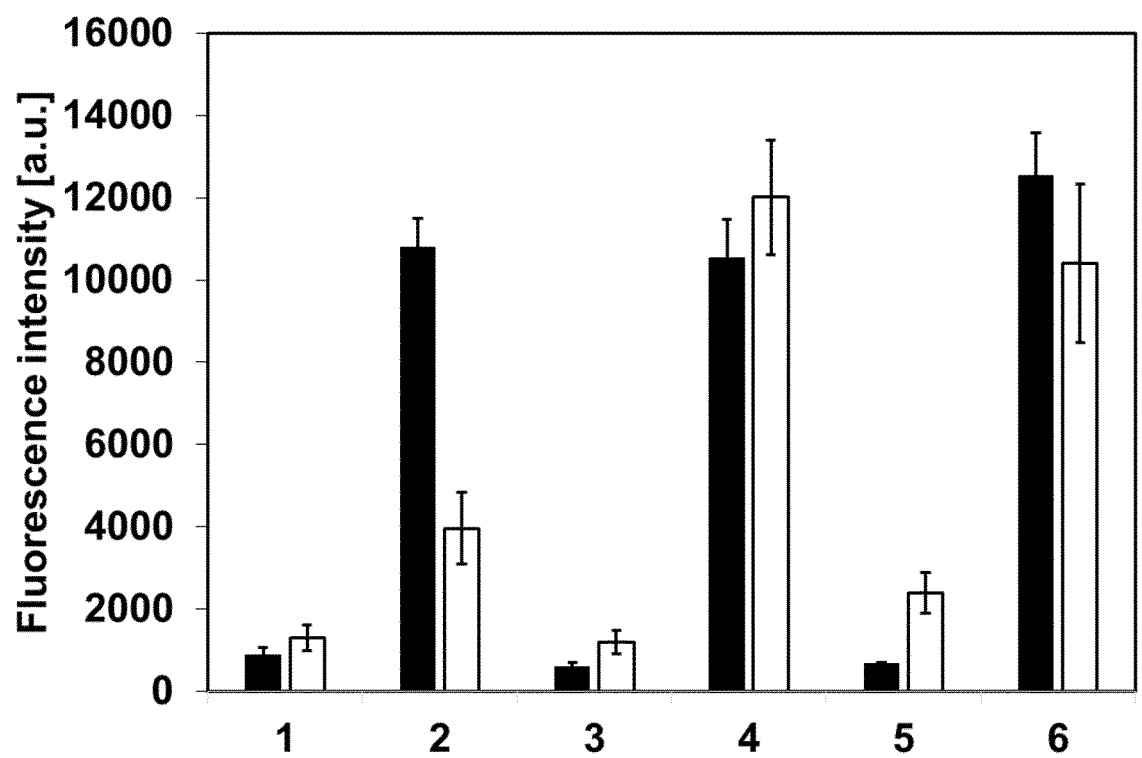

FIG. 16: Fluorescence intensity (Exc: 550 nm, Em: 615 nm) of 350 nM DiI before lyophilization (black bars), and after lyophilization in 96-well plates and reconstitution (white bars).

1: 350 nM DiI in MilliQ water.
2: 350 nM DiI+0.002% (w/v) PS20 in MilliQ water.
3: 350 nM DiI in in 10 mM phosphate buffer, pH 6.0+1% (w/v) mannitol.
4: 350 nM DiI+0.002% (w/v) PS20 in 10 mM phosphate buffer, pH 6.0+1% (w/v) mannitol.
5: 350 nM DiI in in 10 mM phosphate buffer, pH 6.0.
6: 350 nM DiI+0.002% (w/v) PS20 in 10 mM phosphate buffer, pH 6.0.

DETAILED DESCRIPTION OF THE INVENTION

The present invention relates to a new method to quantify polysorbates in a sample, utilizing fluorescent carbocyanine dyes.

As such, the invention relates in a first aspect to a method for the quantification of polysorbates in a sample, comprising the steps of:
a) providing a sample, comprising at least one polysorbate;
b) combining the sample with a carbocyanine dye;
c) measuring fluorescence of the mixture; and
d) correlating said fluorescence with the amount of polysorbate.

Optionally, the sample is a liquid sample and may be used in the method as it is, or after appropriate dilution. Alternatively, the sample may represent a solid material such as a lyophilized composition. In this case, the sample is reconstituted prior to performing step c), or even prior to performing step b). Preferably the sample comprising at least one polysorbate is an aqueous sample or, if provided as a solid material, is reconstituted with an aqueous liquid solvent into an aqueous sample prior to step c) or b). However, any sample allowing fluorescence measurements is suitable. In some embodiments, the sample is a liquid sample in a non-aqueous solvent.

In many cases, the sample additionally comprises one or more proteins, peptides, small molecules and/or other compounds. Preferably the sample comprises an aqueous buffer. Accordingly, in a preferred embodiment the sample comprises a buffering agent.

Suitable buffering agents are known to the person skilled in the art. Some common buffering agents used for samples comprising proteins or peptides include TRIS, HEPES, acetate, histidine, citrate, succinate, glycine and phosphate.

In a most preferred embodiment the sample is an aqueous buffered solution comprising at least one polysorbate.

Alternatively, the sample is a liquid non-aqueous sample. The solvent of the sample might be any suitable solvent. Suitable solvents include, but are not limited to methanol, ethanol or DMSO. Optionally, the sample may contain both water and an organic solvent such as methanol, ethanol, or DMSO.

The sample might optionally comprise one or more further compounds. In preferred embodiments, the sample additionally comprises one or more pharmaceutically or cosmetically active compounds.

In a preferred embodiment, the sample comprises a pharmaceutically active compound. More preferably, the sample comprises a pharmaceutically active compound selected from the group comprising proteins, antibodies, peptides, nucleic acids, virus like particles, cells, bacteria, viruses and small molecules. In a particularly preferred embodiment the sample comprises a protein.

The method is particularly suitable for quantifying polysorbate 20 or 80, but not limited to these polysorbates. The method is suitable for other polysorbates, and possibly other surfactants. In a preferred embodiment, the polysorbate is polysorbate 80 or polysorbate 20.

Figure 1:
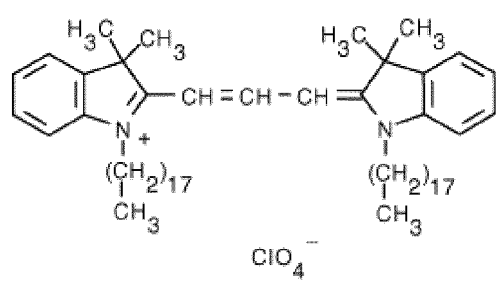
FIG. 1: Structures of the preferred dyes 1'-dioctadecyl-3,3,3',3'-tetramethylindocarbocyanine perchlorate (DiI) (A), 3,3'-Dioctadecyloxacarbocyanine Perchlorate (DiO) (B), 1,1'-Dioctadecyl-3,3,3',3'-Tetramethylindodicarbocyanine 4-Chlorobenzenesulfonate Salt (DiD) (C).
Figure 1:
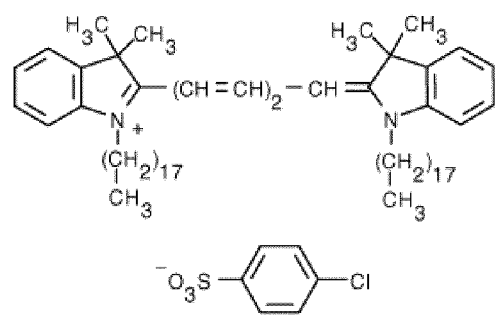
Figure 1:
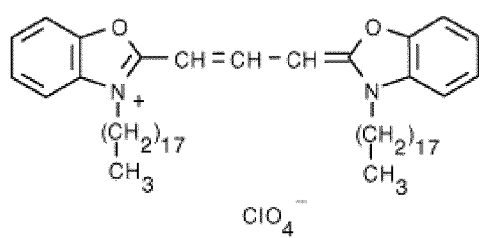

The carbocyanine dye is preferably a lipophile carbocyanine dye. Presently most preferred carbocyanine dyes are the dyes of the so called DiI-family, in particular DiI (1,1'-dioctadecyl-3,3,3',3'-tetramethylindocarbocyanine perchlorate), DiO (3,3'-Dioctadecyloxacarbocyanine Perchlorate) and DiD (1,1'-Dioctadecyl-3,3,3',3'-Tetramethylindodicarbocyanine 4-Chlorobenzenesulfonate Salt). The structures of these dyes are shown in FIGS. 1 A, B and C. A further suitable carbocyanine dye is CM-DiI.

Accordingly, in a preferred embodiment of the invention the carbocyanine dye is a dye selected from the group comprising DiI, DiO, DiD and CM-DiI. In another preferred embodiment, the carbocyanine dye is DiI.

The method of the present invention has the advantage that fluorescence detection is faster and cheaper than methods of the prior art and can be easily automated or semi-automated. The method of the present invention is also more specific than the common NPM assay.

The method might be performed by using any suitable fluorescence detector, preferably a fluorimeter. In some embodiments, this could be a cuvette based fluorimeter. In an alternative embodiment, the method is performed on a plate reader based fluorescence spectrometer. Alternatively, a fluorescence detector can be used and the sample can be introduced into the detector by an HPLC/UPLC system with or without a column.

In general, it is preferred that the fluorescence intensity at a defined wavelength is measured. The inventors were able to identify suitable wavelengths for different carbocyanine dyes allowing the quantification of polysorbates.

Depending on the carbocyanine dye and the polysorbate the excitation wavelength as well as the detected emission wavelength have to be adapted. For example, the inventors found that the fluorescence of DiI shows a blue shift in the presence of polysorbate 20, while the fluorescence spectrum appears to be stable in the presence of polysorbate 80.

In a preferred embodiment of the invention, the carbocyanine dye is DiI, the polysorbate is PS 20 or PS 80, the excitation wavelength is about 550 nm, and the detection wavelength is about 615 nm or alternatively 565 nm.

In further preferred embodiment the carbocyanine dye is DiD, the polysorbate is polysorbate 20 or polysorbate 80, the excitation wavelength is about 644 nm and the detection wavelength is about 665 nm.

In further preferred embodiment the carbocyanine dye is DiD, the polysorbate is polysorbate 20 or polysorbate 80, the excitation wavelength is about 490 nm and the detection wavelength is about 504 nm. In an alternative embodiment, the carbocyanine dye is DiD, the polysorbate is polysorbate 20 or polysorbate 80, the excitation wavelength is about 490 nm and the detection wavelength is about 540 nm.

The inventors found that the determination of polysorbate content using carbocyanine dyes allows rapid and reliable quantification of polysorbates, independent of the presence of degradation products. The inventors also found that the present method provides reliable results in samples further comprising proteins, other excipients and/or silicone oil. Accordingly, the method allows for a fast and rapid quality control of stored samples, e.g. biopharmaceutical drug products in relevant pharmaceutical packaging material such as vials or pre-filled syringes.

A further advantage of the method of the invention is that the method works at different temperatures. It is however preferred that specific temperature ranges are selected for step c), i.e. performing the fluorescence measurement, and for keeping the sample during or after step b) before performing the actual measurement. In particular, the temperatures should preferably be kept relatively constant within series of measurements.

With respect to step c), the fluorescence measurement is preferably performed at a temperature between about 10 and about 40° C., preferably between about 15 and about 37° C., more preferably between about 15 and about 35° C., such as between about 17 and about 30° C., or between about 20 and about 30° C., in particular between about 22 and about 27° C., respectively. In particular preferred embodiments, the method is performed at about 15, 18, 20, 22, 25, 27 or 30° C. In another particularly preferred embodiment, the method is performed at about 20, 25 or 30° C.

Prior to the measurement, the sample is preferably incubated with the dye, which may be understood as an additional step between step b) and step c). It is preferred that the sample is incubated for at least about 1 minute prior to measurement. The incubation time should be selected depending on the temperature at which the incubation occurs. Preferably, the sample is incubated at least about 1, 2, 3, 4, 5, 7, 10, 15, 20 or 30 minutes before measurement. In an alternative preferred embodiment, the sample is incubated for about 10 to 60 minutes, such as for about 10, 20, 30, 40, 50 or 60 minutes. Of course, longer incubation times may also be selected, in particular if the sample is physically and chemically relatively stable at the selected incubation temperature.

In one embodiment, the incubation temperature is selected in the range from about 20 to 45° C. In another preferred embodiment, the incubation temperature is in the range from about 25 to 40° C., or in the range from about 30 to 40° C., such as about 30, 35, 37, or 40° C. Higher incubation temperatures may also be selected, in particular if the sample is physically and chemically relatively stable, or if a short incubation time is selected.

The preferences provided above with respect to the incubation time, the incubation temperature and the temperature of performing the fluorescence measurement should be understood in their combinations. For example, in one of the preferred embodiments, the method of the invention is carried out using an incubation temperature in the range of about 20 to 45° C., an incubation time in the range of about 10 to 60 min, and a measuring temperature in the range of about 10 to 40° C. In another specific embodiment, the incubation temperature is about 37° C., the incubation time is about 30 min, and the measuring temperature is about room temperature or about 23° C. The person skilled in the art will readily be able to identify further measurement conditions for a particular sample.

In addition to the method above, the invention further relates to the use of a carbocyanine dye for the quantification of polysorbates in a sample. In particular, the invention relates to the use of DiI, DiO, DiD or CM-DiI for the quantification of polysorbate in a sample. In a particular embodiment, the invention relates to the use of carbocyanine dye for the quantification of a polysorbate in a sample. In another embodiment, the invention relates to the use of DiI or DiD for quantification of a polysorbate in a sample, preferably polysorbate 20 or 80.

In a further embodiment, the invention relates to the use of DiI for the quantification of a polysorbate in a sample. In a most specific embodiment the invention relates to the use of DiI for the quantification of polysorbate 20 or polysorbate 80 in a sample.

The inventors found that the method can be easily parallelized by the use of 96-well plates and a 96-well plate reader that allows fluorescence analysis. As such, the invention offers a method for rapid and massively parallelized quantification of polysorbates in samples. Accordingly, the method provides a huge improvement for e.g. quality assurance laboratories.

Therefore, the invention also relates to a well plate comprising a carbocyanine dye. In a preferred embodiment, the invention relates to a well-plate, wherein at least one of the wells comprises a defined amount of a carbocyanine dye. In one embodiment, the invention relates to a well plate, wherein a plurality the wells comprise a defined amount of carbocyanine dye and wherein at least one well additionally comprises a defined amount of a polysorbate.

In a preferred embodiment, the plate is a 96 well plate. However, any other type of well-plate is suitable as well. At least some of the wells of the well plate comprise an amount of carbocyanine dye. It is also preferred that every well of the plate comprises the same amount of carbocyanine dye. In some embodiments of the invention, the plate comprises some wells additionally comprising a defined amount of a polysorbate. In this context, the same preferences with respect to the selection of the carbocyanine dye apply as have been described above for the method according to the invention.

Preferably, the dye in the wells and the optional further components such as polysorbates are provided in lyophilized form in the wells. In an alternative embodiment of the invention, the wells comprise a liquid solution comprising the dyes and optionally in some wells also a defined amount of polysorbate. Aside from lyophilization, other methods for drying may be used. The skilled person is aware of suitable methods.

In a particular preferred embodiment, the invention relates to a well plate comprising:
a) a set of wells wherein each well of the set comprises a carbocyanine dye in a defined amount; and
b) a set of wells wherein each well of the set comprises a carboycyanine dye and a defined amount of polysorbate.

As used herein, a set (or subset) of wells is a subset of the wells of a well plate; a set (or subset) comprises at least two wells. Preferably, the wells comprising a carbocyanine dye and a defined amount of polysorbate comprise different amounts of polysorbate; more preferably, said set of wells allows for the generation of a polysorbate calibration curve.

In some embodiments, the well plate additionally comprises empty wells or wells without carbocyanine dye, which might act as blanks.

In a preferred embodiment, said plate comprises one or more sets of wells comprising a carbocyanine dye and a defined amount of polysorbate as defined above. In these cases, each set of wells may comprise the same or a different polysorbate.

In some embodiments, the wells comprise lyophilized compositions. In these cases, it is preferred that the plate comprises additionally buffering and/or stabilizing compounds in the wells or in the composition in the wells.

The inventors found, that compositions to provide a well plate comprising wells with a carbocyanine dye, wherein some wells additionally comprise polysorbate, can be prepared as aqueous compositions, which are filled in the wells and can be subsequently lyophilized.

The end user only needs to add his sample to a defined set of wells and fill the remaining wells with a defined amount of water.

Said aqueous compositions may only comprise a defined amount of carbocyanine dye and optional polysorbate, depending on the set of wells. This allows for a sufficient recovery of fluorescence signal after reconstitution of the composition.

The inventors found that an optimal recovery of fluorescence signal after reconstitution of the lyophilized compositions may be obtained, if the compositions further comprises a buffer and optionally a stabilizer, preferably a saccharide, more preferably mannitol.

In a preferred embodiment, said stabilizer is present in a concentration of up to 10% (w/v). In a specific embodiment, said stabilizer is present in a concentration between 0.1% to 10% (w/v). Preferably, said stabilizer is present in a concentration of up to 5% (w/v), specifically 0.5 to 5% (w/v). In a particular preferred embodiment, the stabilizer is present in a concentration of about 1% (w/v)

Any buffer may be suitable, buffers for routine application are known to the skilled person. Preferably, said buffer does not provide a fluorescence signal in addition to the DiI. One suitable buffer is phosphate buffer.

In a further aspect, the invention relates to a kit for the quantification of a polysorbate in a sample comprising:
a) a carbocyanine dye;
b) a diluent buffer;
c) optionally, a set of standard solutions each comprising a defined amount of polysorbate.

In some embodiments of the invention, the carbocyanine dye is in a cuvette. More preferably, said kit comprises at least one cuvette comprising a defined amount of carbocyanine dye. In a specific embodiment, said cuvette is a microcuvette.

The kit may optionally also comprise further compounds, in particular instructions for use. In particular embodiments, the kit comprises a carbocyanine dye selected from DiI, DiD, DiO, CM-DiI.

Most preferably, the kit comprises DiI. In some embodiments, the diluent buffer is a concentrated buffer.

The standard solution might be ready to use solutions, or solutions to dilute. Preferably, the standard solutions are concentrated solutions. In some embodiments, the kit comprises different standard solutions in different solvents.

The standard solutions might be adapted to different base applications. In particular the standard solutions comprise different polysorbates in defined amounts. Preferably the standard solutions comprise polysorbate 20, polysorbate 80 or mixtures thereof.

In a preferred embodiment of the invention, said kit comprises a well-plate as defined above.

EXAMPLES

Methods
Preparation of PS-Calibration Curves

PS20 and PS80 stock solutions (1.0% (w/v) prepared in water) were prepared and stored at −20° C. in 1 mL aliquots. These stocks were used for all the experiments reported. PS calibration curves were prepared by performing serial dilutions—in water or buffer—within a range of 0.0002 to 0.007% (w/v), approximately. As a control, a sample only containing water or the corresponding buffer was used.

The Fluorescence-Assay

The DiI-Vybrant™ stock solution is a 1 mM solution of DiI in ethanol. An intermediate stock solution (at a concentration of 20 µM) in water was prepared by adding 2 µL of the initial dye solution to 98 µL of Milli-Q water. This DiI-working solution (DiI-WS) was freshly prepared before adding it to the samples. DiI was added to the different samples for the PS calibration curve. The final concentration of DiI in the analysed samples was 357 nM. After the addition of the dye to the samples, there were immediately vortexed and incubated at 37° C. for 30 min protected from light. The DiD-Vybrant™ (1 mM solution of DiD in ethanol) samples were prepared and handled, analogously.

Fluorescence Measurements Cuvette System for DiI

A FP-8500 fluorometer (Jasco, Germany) and a 10×2 mm quartz cuvette were used for the measurements. The excitation wavelength was set to 550 nm (bandwidth 2.5 nm), whereas emission was recorded in the range of 560-620 nm (bandwidth: 2.5 nm, interval: 1 nm, speed: low, sensitivity: high, number of accumulations: 1). Water was always used as a reference. All the experiments were carried out at 21° C. (thermostatized instrument).

Fluorescence Measurements Plate Reader System

For the well-plate based measurements, a plate reader (Tecan Safire$^2$; Tecan Group AG, Switzerland) was used. The excitation wavelength for DiI was fixed to 550 nm (bandwidth: 5 nm) and emission was collected in the range of 560-620 nm (bandwidth: 5 nm; emission wavelength step size: 1 nm). The number of reads was set to 20. The gain and the z-position were determined by the device based on the well containing the highest concentration of PS. The gain was finally fixed to 120 and the z-position was adjusted to 8100 µm. The measurements were carried out in duplicates using a black 96-well plate with a flat bottom. A final volume per well was 200 µL. Regular as well as low-binding-plates were tested. All the experiments were conducted at 23° C., approximately (non-thermostatized instrument).

UV/Vis-Measurements

UV/Vis measurements were performed utilizing the Safire 2 Multimode Reader. The solutions provided by performing the dilution series and further samples were investigated using the corresponding solvent (water/buffer) as a blank. The absorption spectra, resulting from 2 accumulations, were recorded within the range of 270-999 nm. For this experiment, a 96-well plate was employed with a final volume per well of 150 µL.

Fluorescence Profiling of PS20 in the Presence of DiI or DiD

Figure 2:
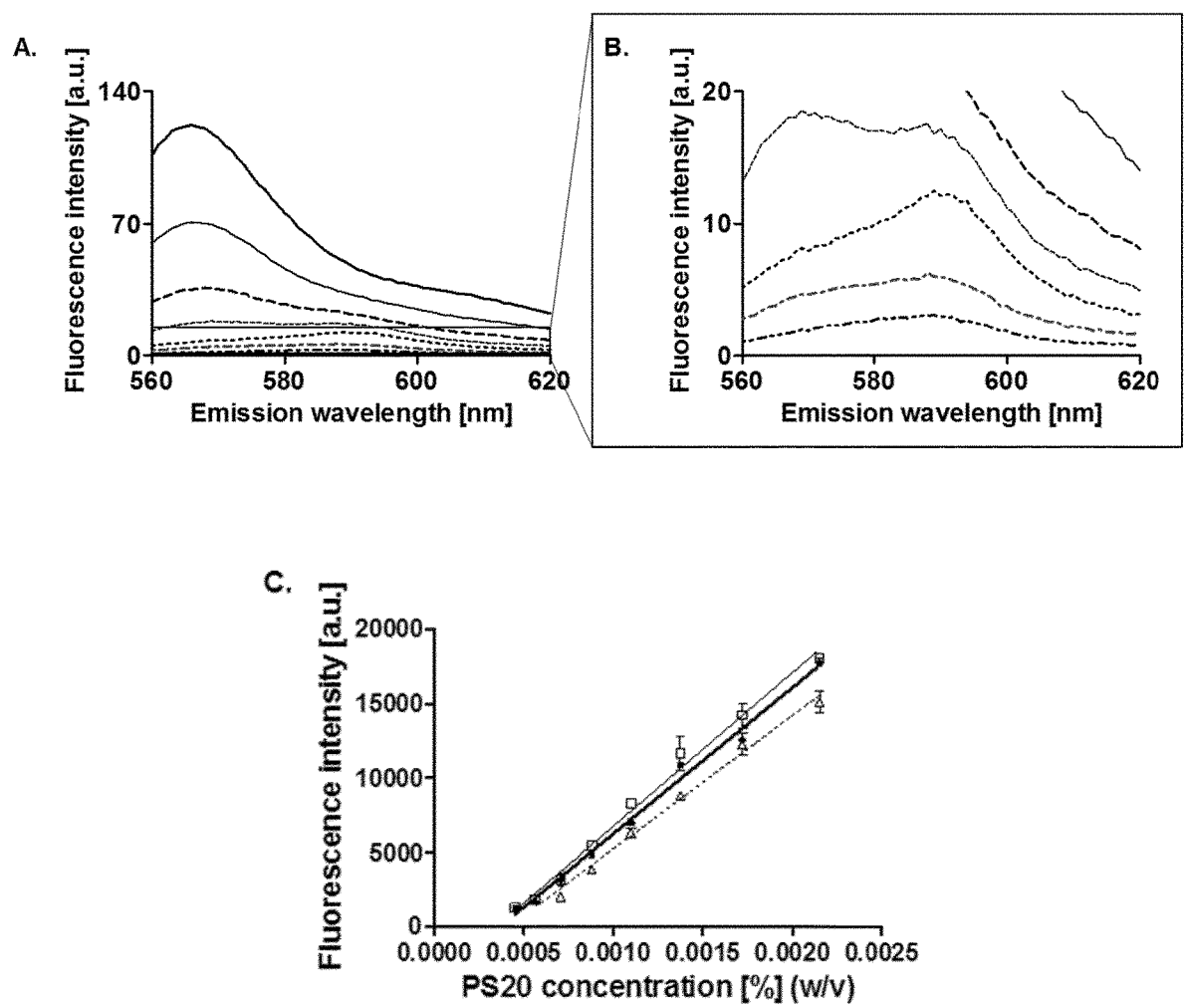
FIG. 2: Fluorescence emission properties of polysorbate 20 (PS20) in the presence of DiI.

The fluorescence properties of PS20 were evaluated in the presence of DiI using a cuvette based fluorimeter. For this purpose, samples covering a concentration range of 0.0002 to 0.0025% (w/v) were prepared. The results are illustrated in FIGS. 2A, 2B and 2C. The maximum fluorescence intensity was obtained at approximately 590 nm. It was shifted to lower wavelengths (-565 nm) at PS20 concentrations above 0.0005% (w/v).

The fluorescence signal at 615 nm showed consistent results when performing repetitive measurements. Apart from that, the intensity at the aforesaid wavelength was proportional to the concentrations tested—as presented in FIG. 1C.

Based on these results, the emission wavelength for PS20 quantification was fixed to 615 nm. In order to check for the inner filter effect, the absorption at the emission and excitation wavelength was measured in further experiments. Based on the experiments the concentrations of DiI and PS were selected to avoid inner filter effect during fluorescence analysis.

The same experiments were performed with DiD and PS20 with similar results, see FIGS. 3A, 3B and 3C. The emission wavelength for DiD was selected to be 665 nm.

Fluorescence Profiling of PS80 in the Presence of DiI and DiD

The fluorescence assay shown to be applicable for PS20 quantification, was also tested for PS80. First, the corresponding fluorescence profiles were measured in a fluorimeter with the parameters being set as seen for PS20 for DiI and DiD.

Different graphs were plotted based on the data provided. FIGS. 4A, 4B, 5A and 5B present an overview of the fluorescence intensities obtained at 615 nm (DiI) or 665 nm (DiD) of all the samples measured. Sample calibration curves for 0.00045 to 0.00114% (w/v) PS80 can be seen in FIGS. 4C and 5C.

Influence of Silicone Oil on DiI Fluorescence

In a further experiment the influence of other compounds in the composition on the DiI fluorescence was measured. In a first measurement in a fluorimeter the influence of silicon oil droplets in the sample was analysed.

For this experiment, the fluorescence of DiI in an aqueous solution was measured and compared to the fluorescence of DiI in an aqueous solution with 0.002% (w/v) and 0.03% (w/v) silicone oil was tested. The results can be seen in FIG. 6.

The results show that silicone oil droplets do not significantly alter DiI fluorescence.

DiD/DiI Fluorescence Measurements and Sample Analysis in a Plate Reader

In order to test the possibility to parallelize the method, fluorescence measurements with DiD and PS20, as well as DiI and PS80 were performed in a plate reader (Tecan Safire²; Tecan Group AG, Switzerland).

A calibration curve for PS20 and DiD was measured and a sample comprising 0.00175% (w/v) PS20 were measured using the plate reader. The results are shown in FIG. 7 and summarized in table 1.

TABLE 1

PS20 concentrations [%] (w/v) and recoveries [%] of PS20-concentration measurements for protein-free samples in 10 mM phosphate buffer (pH 6.0) containing 0.00175% (w/v) PS20. A PS20-DiD-calibration curve was used for quantification.

| Sample | PS20 concentration [%] (w/v) and recovery [%] * when interpolated in PS20-DiD-calibration curve without protein |
|---|---|
| No protein | 0.00163 |
| PS20 0.00175% (w/v) | 93.0 |

* recovery = calculated PS20 concentration/expected PS20 concentration*100 expected PS20 concentration: 0.00175% (w/v)

A further calibration curve for PS80 and DiI was measured and a sample comprising 0.0007% (w/v) PS20 were measured using the plate reader. The results are shown in FIG. 8 and summarized in table 2.

TABLE 2

PS80 concentrations [%] (w/v) and recoveries [%] of PS80-concentration measurements for protein-free samples in 10 mM phosphate buffer (pH 6.0) containing PS80 at 0.00126% (w/v) and 0.00112% (w/v). A PS80-DiI-calibration curve was used for quantification.

| Sample | PS80 concentration [%] (w/v) and recovery [%] * when interpolated in PS80-DiI-calibration curve without protein |
|---|---|
| No protein | 0.00128 |
| PS80 0.00126% (w/v) | 100.8 |
| No protein | 0.00106 |
| PS80 0.00112% (w/v) | 94.6 |

* recovery = calculated PS80 concentration/expected PS80 concentration*100 expected PS80 concentration: 0.0007% (w/v)

Influence of Protein on PS Quantification by DiI

In a further experiment the influence of the presence of two different monoclonal antibodies (IgG1 and IgG2) as representative proteins in samples on PS20 quantification by DiI was tested. A calibration curve, as well as some PS20 containing samples were measured on a plate-reader. The results can be seen in FIG. 9 and table 3.

TABLE 3

PS20 concentrations [%] (w/v) and recoveries [%] of PS20-concentration measurements for 0, 5 and 15 mg/mL IgG1 and IgG2 solutions in 10 mM phosphate buffer (pH 6.0) containing PS20 at 0.002% (w/v). PS20-DiI-calibration curves (prepared without protein --●-- and with 15 mg/mL IgG1 --□--) at 615 nm, after excitation at 550 nm, were measured in a plate-reader and used for quantification, respectively.

| Samples | PS20 concentration [%] (w/v) and recovery* based on interpolation in DiI calibration curve without protein | PS20 concentration [%] (w/v) and recovery* based on interpolation in DiI calibration curve with 15 mg/mL IgG1 |
|---|---|---|
| Sample 1: 0.002% (w/v) PS20, no protein | 0.0021 / 104.9 | 0.0023 / 113.1 |
| Sample 2: 0.002% (w/v) PS20, IgG1 5 mg/mL | 0.0020 / 98.9 | 0.0022 / 107.1 |
| Sample 3: 0.002% (w/v) PS20, IgG1 15 mg/mL | 0.0021 / 103.4 | 0.0022 / 111.5 |
| Sample 4: 0.002% (w/v) PS20, IgG2 5 mg/mL | 0.0018 / 92.3 | 0.0020 / 100.5 |
| Sample 5: 0.002% (w/v) PS20, IgG2 15 mg/mL | 0.0019 / 96.1 | 0.0021 / 104.3 |

*recovery = calculated PS20 concentration/expected PS20 concentration*100 expected PS20 concentration: 0.002% (w/v)

Influence of Incubation Time on DiI Fluorescence

In a further experiment it was analysed if a pre-measurement incubation time has an influence on the DiI fluorescence intensity in PS containing samples. Samples were prepared as above and measured directly or after 15 or 30 minutes of incubation. The results are shown in FIG. 10. As the figure shows, the influence of incubation time on the resulting DiI fluorescence and PS20 calibration curves is negligible.

Influence of Plate Shaking and Temperature During Incubation on DiI Fluorescence In an additional experiment, the influence of incubation temperature on the fluorescence measurement and shaking the plates during incubation was analysed to determine specific requirements for assays performed in 96 well plates.

One set of samples (PS20 calibration curve) was prepared, and aliquots thereof were incubated for 15 minutes (i) with or (ii) without shaking at 37° C., and (iii) at room temperature without shaking.

The results of this experiment are shown in FIG. 11. They clearly indicate that neither shaking nor the temperature during incubation had an influence on the calibration curve.

Influence of Different Dye Batches

In further experiment the reproducibility of the results with different batches of DiI dye was analysed. In this experiment three samples (PS20 calibration curves) were analysed with DiI of different batches from the same supplier. All samples were analysed after 15 min incubation at 37° C.

The results are shown in FIG. 12. The results show that they are comparable, independent of the dye batch.

Applicability of the DiI Assay for PS20 and PS80 from Different Suppliers

A similar experiment was performed using PS20 or PS80 from different suppliers. Polysorbates of three different suppliers were analysed in the same way as before by DiI. The results are shown in FIGS. 13 and 14. It is again evident that the results are comparable, independent of PS20 or PS80 supplier. As such, a single PS calibration curve may be used to quantify PS in a sample independent of the original supplier Influence of Different Proteins on DiI Fluorescence In a further experiment, samples comprising 0.006% w/v polysorbate 20 or polysorbate 80 and different proteins (IgG1, Fc fusion protein or IgG) in varying concentrations were measured. The results are shown in FIG. 15 and indicate that the presence of the tested proteins has no influence on the fluorescence measurement.

Influence of Lyophilization on DiI Fluorescence

In one experiment several samples were prepared, filled into 96-well plates and the DiI fluorescence intensity was measured. Afterwards, the samples were lyophilized in 96-well plates, subsequently reconstituted and the fluorescence intensity was measured after reconstitution. The following samples were prepared and measured:

1: 350 nM DiI in MilliQ water.
2: 350 nM DiI+0.002% (w/v) PS20 in MilliQ water.
3: 350 nM DiI in in 10 mM phosphate buffer, pH 6.0+1% (w/v) mannitol.
4: 350 nM DiI+0.002% (w/v) PS20 in 10 mM phosphate buffer, pH 6.0+1% (w/v) mannitol.
5: 350 nM DiI in in 10 mM phosphate buffer, pH 6.0.
6: 350 nM DiI+0.002% (w/v) PS20 in 10 mM phosphate buffer, pH 6.0.

The results are shown in FIG. 16. The results show that it is possible to prepare plates with lyophilized compositions for this assay, to retain the DiI fluorescence properties after lyophilization and reconstitution. The results indicate that the use of a buffered composition comprising a stabilizer such as mannitol improves the results.

The invention claimed is:

1. A method for the quantification of a polysorbate in a sample, comprising the steps of:
   a) providing a sample, comprising at least one polysorbate;
   b) combining the sample with a carbocyanine dye;
   c) measuring fluorescence of the mixture; and
   d) correlating said fluorescence with the amount of polysorbate.

2. The method according to claim 1, wherein the carbocyanine dye is selected from the group consisting of 1,1'-dioctadecyl-3,3,3',3'-tetramethylindocarbocyanine perchlorate (DiI), 3,3'-Dioctadecyloxacarbocyanine Perchlorate (DiO), 1,1'-Dioctadecyl-3,3,3',3'-Tetramethylindodicarbocyanine 4-Chlorobenzenesulfonate Salt (DiD) and CM-DiI.

3. The method according to claim 2, wherein the carbocyanine dye is 1,1'-dioctadecyl-3,3,3',3'-tetramethylindocarbocyanine perchlorate (DiI).

4. The method according to claim 1, wherein the polysorbate is selected from polysorbate 20 or polysorbate 80.

5. The method according to claim 1, wherein the sample additionally comprises a pharmaceutically active compound.

6. The method according to claim 5, wherein the pharmaceutically active compound is a protein.

7. The method according to claim 1, wherein the sample additionally comprises a cosmetic compound.

8. The method according to claim 1, wherein the sample is lyophilized, and reconstituted in a solvent prior to step c).

9. A well plate, wherein a plurality of wells comprises a defined amount of a carbocyanine dye and wherein at least one well of said plurality of wells additionally comprises a defined amount of polysorbate.

10. The well plate according to claim 9, wherein the carbocyanine dye is selected from the group consisting of 1,1'-dioctadecyl-3,3,3',3'-tetramethylindocarbocyanine perchlorate (DiI), 3,3'-Dioctadecyloxacarbocyanine Perchlorate (DiO), 1,1'-Dioctadecyl-3,3,3',3'-Tetramethylindodicarbocyanine 4-Chlorobenzenesulfonate Salt (DiD) and CM-DiI.

11. The well plate according claim 10, wherein the carbocyanine dye is 1,1'-dioctadecyl-3,3,3',3'-tetramethylindocarbocyanine perchlorate (DiI).

12. The well plate according to claim 9, wherein the well plate comprises a subset of wells, wherein each well of the subset additionally comprises a defined amount of polysorbate.

13. The well plate according to claim 9, wherein at least one well additionally comprises a buffer.

14. The well plate according to claim 13, wherein the buffer is a phosphate buffer.

15. The well plate according to claim 9, wherein at least one of the wells additionally comprise a stabilizer.

16. The well plate according to claim 15, wherein the stabilizer is a saccharide.

17. The well plate according to claim 16, wherein the saccharide is mannitol.

18. The well plate according to claim 9, wherein the well plate comprises at least two different subsets of wells, each well of each of the two sets comprises a composition comprising:
   a) a defined amount of a carbocyanine dye;
and wherein each well of at least one subset of wells additionally comprises in the composition:
   b) a buffer; and
   c) a stabilizer;
   d) a defined amount of polysorbate.

19. The well plate according to claim 18, wherein the composition is a lyophilized composition.

* * * * *

UNITED STATES PATENT AND TRADEMARK OFFICE
CERTIFICATE OF CORRECTION

PATENT NO. : 11,662,312 B2
APPLICATION NO. : 16/624730
DATED : May 30, 2023
INVENTOR(S) : Martos-Sánchez et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 313 days.

Signed and Sealed this
Twenty-eighth Day of January, 2025

Coke Morgan Stewart
*Acting Director of the United States Patent and Trademark Office*